(12) United States Patent
Friedlander

(10) Patent No.: US 8,236,256 B2
(45) Date of Patent: Aug. 7, 2012

(54) APPARATUS AND METHOD FOR EFFICIENT AND PRECISE TRANSFER OF LIQUIDS

(76) Inventor: Thomas Friedlander, Rye Brook, NY (US)

( * ) Notice: Subject to any disclaimer, the term of this patent is extended or adjusted under 35 U.S.C. 154(b) by 253 days.

(21) Appl. No.: 12/767,900

(22) Filed: Apr. 27, 2010

(65) Prior Publication Data

US 2011/0262320 A1 Oct. 27, 2011

(51) Int. Cl.
*B01L 3/02* (2006.01)
(52) U.S. Cl. ........ 422/501; 422/509; 422/511; 422/516; 422/521; 73/863.32; 73/864; 73/864.11
(58) Field of Classification Search .................. 422/501, 422/509, 511, 516, 521, 63, 66–67; 73/863.32, 73/863.52, 864, 864.01, 864.11
See application file for complete search history.

(56) References Cited

U.S. PATENT DOCUMENTS

| | | | | |
|---|---|---|---|---|
| 3,918,910 | A * | 11/1975 | Soya et al. ..................... | 422/66 |
| 5,435,197 | A | 7/1995 | Telimaa et al. | |
| 5,897,034 | A * | 4/1999 | Sewell ........................ | 222/386 |
| 6,254,832 | B1 | 7/2001 | Rainin et al. | |
| 6,431,015 | B1 | 8/2002 | Hodac et al. | |
| 6,579,497 | B2 * | 6/2003 | Woodward ..................... | 422/66 |
| 6,749,812 | B2 | 6/2004 | Cronenberg et al. | |
| 6,814,936 | B1 | 11/2004 | Enhorning | |
| 6,923,938 | B2 | 8/2005 | Cote et al. | |
| 7,638,023 | B2 * | 12/2009 | Marquant .............. | 204/403.02 |
| 7,988,934 | B2 * | 8/2011 | Balmer ....................... | 422/509 |
| 2002/0012613 | A1 | 1/2002 | Scordato et al. | |
| 2003/0194349 | A1 * | 10/2003 | Carey et al. ..................... | 422/63 |
| 2005/0079105 | A1 * | 4/2005 | Hunter et al. .................. | 422/100 |
| 2005/0118069 | A1 | 6/2005 | Solotareff et al. | |
| 2005/0244303 | A1 | 11/2005 | Ingenhoven et al. | |
| 2007/0025882 | A1 | 2/2007 | Zuppiger et al. | |

* cited by examiner

*Primary Examiner* — Brian R Gordon
(74) *Attorney, Agent, or Firm* — UCONN IP Law Clinic; Lily Neff; Yang Gao

(57) ABSTRACT

A device for automatically aspirating and/or dispensing liquids with precision, comprising a housing having an opening at a lower end with a fixed tip protruding out of the lower end; an interchangeable cartridge disposed inside the housing, the cartridge having a holding frame and a spool of tubing provided in the frame such that one end of the tubing is aligned with the tip; and an actuator enabled to automatically extrude part of the tubing so as to accommodate a preselected volume of liquid, aspirate and/or dispense the liquid through the extruded tubing, and disconnect the extruded tubing from the device.

17 Claims, 6 Drawing Sheets

APPARATUS AND METHOD FOR EFFICIENT AND PRECISE TRANSFER OF LIQUIDS

FIELD OF INVENTION

This invention relates generally to a method and apparatus for transferring liquids of reagents and samples, and more particularly to an improved pipette having an ergonomic design that optimizes accuracy and efficiency.

BACKGROUND OF THE INVENTION

Pipetting systems are widely used in the pharmaceutical industries, as well as in industries dealing in cosmetics, food and beverage production. These systems are also used in clinical research applications. These systems are used to aspirate and dispense relatively small and/or preselected volumes of liquids from one receptacle to another. Conventional pipetting systems generally include a housing that comprises a piston and a plunger to enable dispensing and aspiring of liquids. A rigid plastic tip is usually also attached to the pipette, at one end, to enable the transfer and to prevent contamination of liquids by successive samples, often disposable plastic tips are used. Unfortunately, conventional pipetting systems have several shortcomings and problems associated with their use.

One problem associated with the use of these systems deal with the operation of transferring liquids from one receptacle into another. Operations of conventional piptes need to be manually performed by applying force to the plunger head, usually with a thumb or a finger, in order to actuate the piston. Even if the plunger can be motorized, the user still needs to tightly grip the pipette, especially when mounting and removing the tip from the tip holder. Since repetitive and frequent operation of the pipette is required every day, continued use of these systems contributes to an increased risk of hand and shoulder injuries and may lead to other related ailments often associated with repetitive stress injuries.

A second problem associated with the use of conventional pipettes is the accuracy and range of volume that can be transferred with such devices. Precise measurements of liquids are difficult to achieve and different transfer of volumes in a wide range cannot be accomplished by a single device and therefore different devices and different corresponding tips have to often be utilized. Even then, accuracy is difficult to achieve using current disposable tips as they need to be made from rigid materials in order to allow for proper mounting of the tip to the device. Unfortunately, the mounting of such tips still leaves a large air gap between the piston of the device and the liquid being aspirated and/or dispensed. This gap subsequently affects the accuracy of the actual volume being transferred. The effect of inaccurate dispensation/aspiration is more significant and noticeable when small volumes of liquid are being transferred. As with regards to range of volume supported, the changing of the devices and/or their associated tips affects the overall labor and cost requirements which can burden the overall operation.

A related problem associated with using prior art pipettes that require disposable plastic tips is environmental concerns. As environmental awareness has increased, a great deal of attention is being paid to reducing the environmental impact by minimizing the need to utilize disposable plastic tips.

Consequently, it is desirable to have an improved apparatus and method which can overcome some of the problems associated with the prior art systems as enumerated.

SUMMARY OF THE INVENTION

The shortcomings of the prior art are overcome and additional advantages are provided through the provision of a device and related method for automatically aspirating and/or dispensing liquids with precision. The device, in one embodiment, comprises a housing having an opening at a lower end with a fixed tip protruding out of this lower end. It also comprises an interchangeable cartridge disposed inside the housing having a spool of plastic tubing such that one end of the tubing is positioned to align with the center of the fixed tip and an actuator. The actuator is enabled to automatically extrude part of the tubing so as to accommodate a preselected volume of liquid and aspirate and/or dispense the liquid through the extruded tubing. This embodiment further comprises a control circuit operable to drive the actuator. The control circuit has a plurality of power sources, actuateable control keys in electrical communication with the control circuit and enabled to preselect modes of operation and volumes of liquid to be aspirated and/or dispensed, a display for displaying numbers and/or alpha-numerical characters, and a memory component for storing data accessible by the control circuit to enable preselected operations.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following description taken in connection with the accompanying drawings in which:

DETAILED DESCRIPTION

Figure 1:
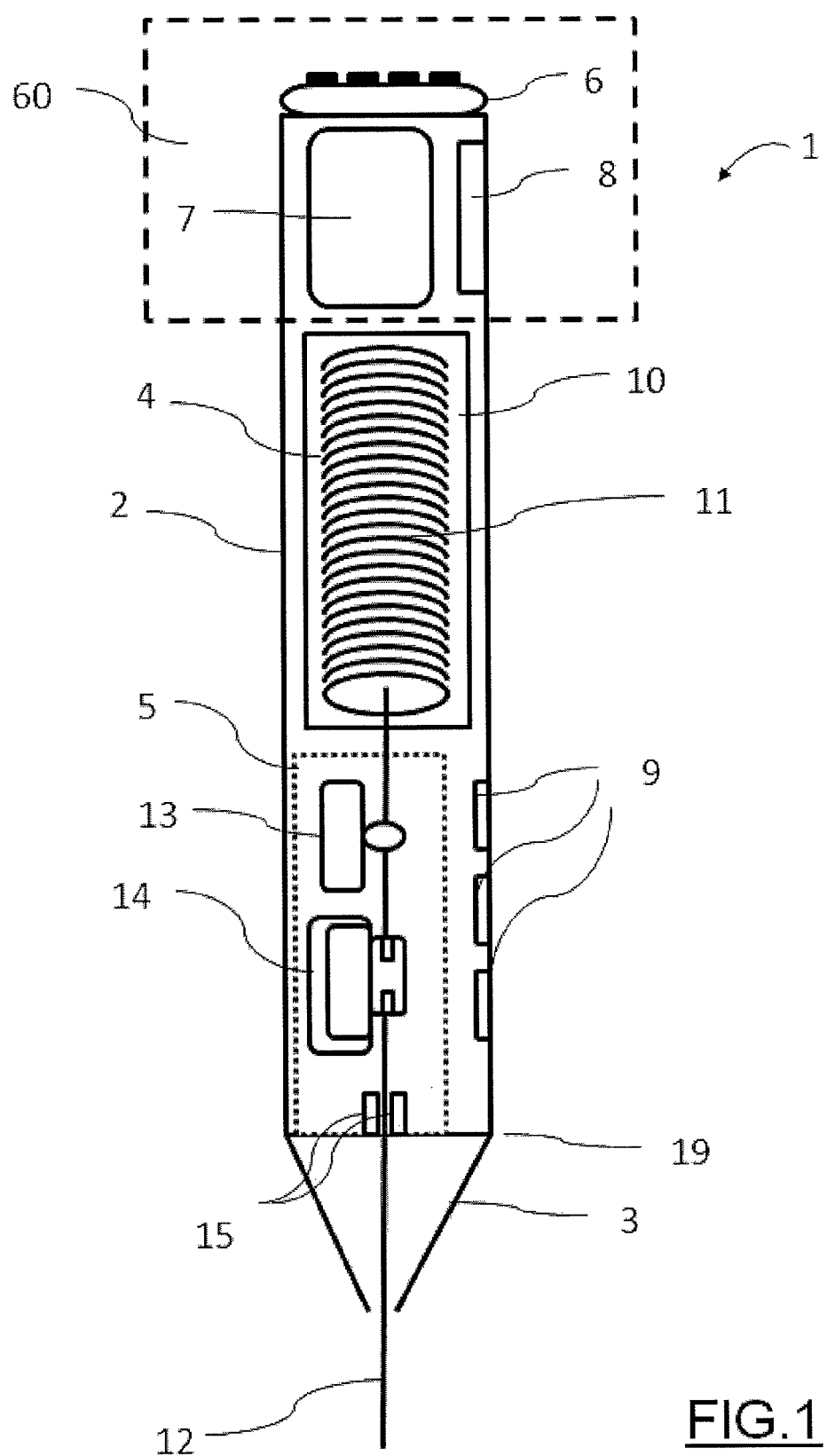
FIG. 1 is a schematic illustration providing a sectional view of one embodiment of the present invention.

FIG. 1 is a cross sectional depiction of one embodiment of the present invention illustrating a liquid transferring device as referenced by numeral 1. The liquid transferring device 1 comprises a housing 2 having an opening at its lower end 19. The housing shown in FIG. 1 has a generally cylindrical shape, however, other alternate shapes and structures can also be provided as known to those skilled in the art in alternative embodiments and the cylindrical shape of the housing 2 in FIG. 1 is only provided by way of example.

In one embodiment, as shown in FIG. 1, the lower end 19 of the housing 2 can further include a tip, preferably having a substantially conical shape or other such structure as known to those skilled in the art. In this embodiment, the conical shape is chosen to aid structural support to tubing that can be extruded, as is described latter in this specification. As shown, the conical tip is referenced by numeral 3. In this embodiment, the tip 3 is elongated in design, extending from the housing 2 such that the tip 3 generally protrudes out of the lower end 19.

The housing 2 also comprises a cartridge referenced as 4. In one embodiment, as shown the cartridge 4 is disposed at an opposing end from the tip 3. In a preferred embodiment, the cartridge 4 is an interchangeable cartridge which further comprises a holding frame 10 and one or more spool(s) of tubing 11, the spool(s) being disposed in the frame 10. The spool 11, in one embodiment, is positioned such that one end of the tubing in the spool 11 is enabled to align with and be extruded out of the conical tip 3, with the extruded portion shown by numerals 12. Tubing in spool 11 can have a variety of inner diameters selectively interchangeable depending on the desired volume of liquid to be handled. In addition, tubing in spool 11 can be fabricated of different materials in order to accommodate a range of materials and liquids that need to be transferred. For example, plastic tubing may be used in relation to a first material but such tubing may not be suitable to be used with certain type of concentrated acids and a material replacement needs to be made to handle the latter. In some embodiments of the invention the inner wall or surface of the tubing in spool 11 can be pretreated with selective reagents. For example, the tubing can be pretreated so as to provide pre-coating with antibodies or other materials as known to those skilled in the art. Pretreatment of tubing can provide a number of different advantages as appreciated by those skilled in the art. For example, pretreatment can minimize risk of contamination or alternatively can be used to reduce the number of processing steps required. The length of tubing can also be selective. The latter can easily replace the need for disposable tips such as used in traditional devices, with the added advantage of providing a continuous supply and adjustable length of tubing (and tips) and allowing a wide range of operations with a single device. The tubing in spool 11 is also able to be pressed to a flat form when rolled in the spool 11, and is able to form a tubular form when extruded.

Figure 3:
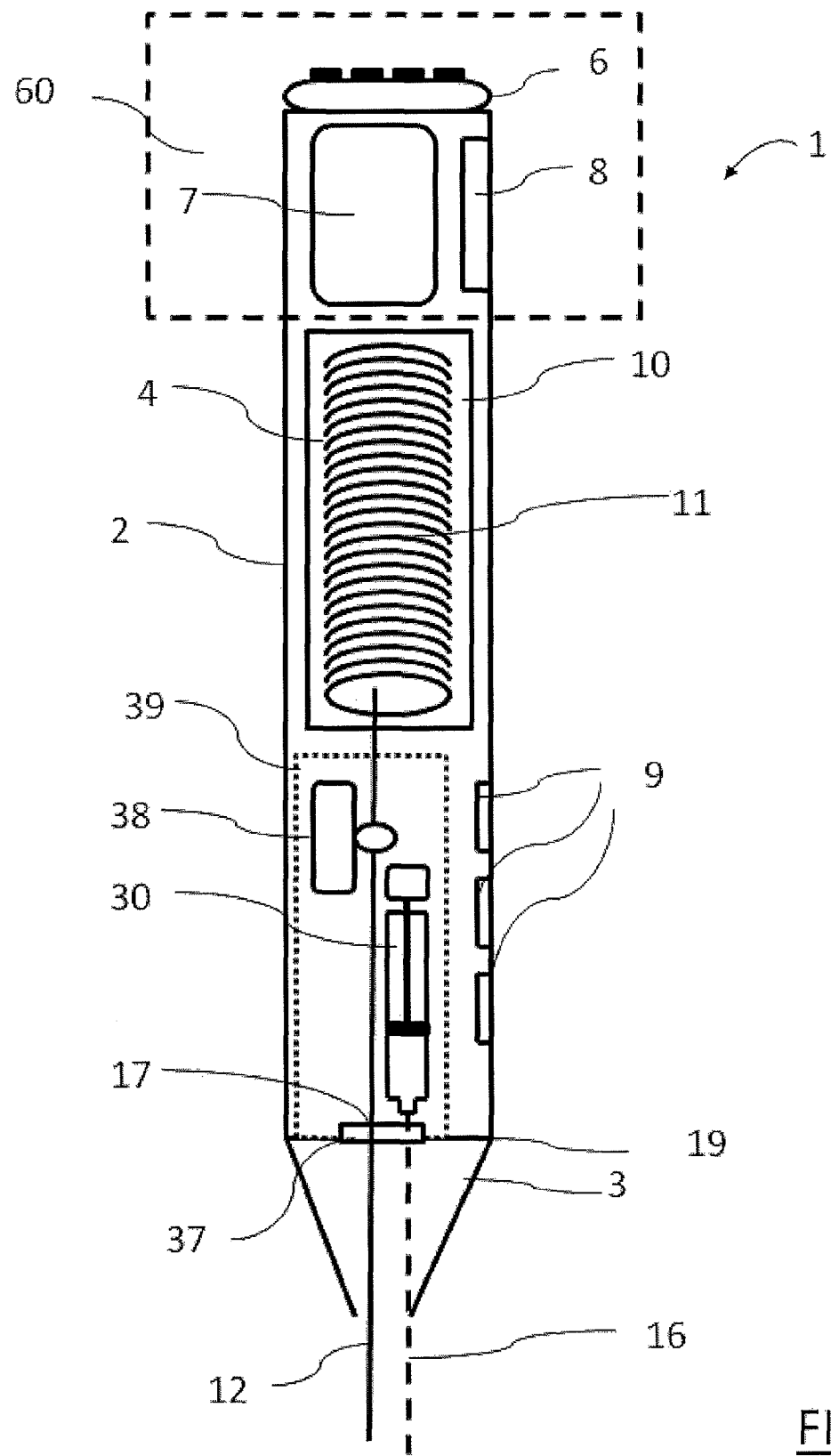
FIG. 3 is a schematic illustration providing a sectional view of an alternate embodiment of the present invention.

In the embodiment of FIG. 1, an actuator 5 is also provided and disposed in the housing 2 below the interchangeable cartridge 4. The actuator 5, in one embodiment can have a plurality of components. In FIG. 1 shown, the actuator 5 includes three components: namely a mechanism 13, a pump 14, and a cut-off component 15. Different components or additional ones can be used/substituted or removed in other environments. In the embodiment shown in FIG. 1, the pump 14 is a peristaltic pump. However, other types of pumps can be utilized as known by those skilled in the art in alternate embodiments. For example, as will be discussed later, in another embodiment as shown in FIG. 3, a syringe pump is provided. In FIG. 1 shown, mechanism 13 is enabled to automatically extrude a portion of tubing from spool 11. In one embodiment, the spool can then be dissected, cut, perforated, pinched etc. such that a desired amount of tubing length is extruded and at least a certain amount of the extruded portion is isolated and/or sealed off from the spool 11.

Figure 2:
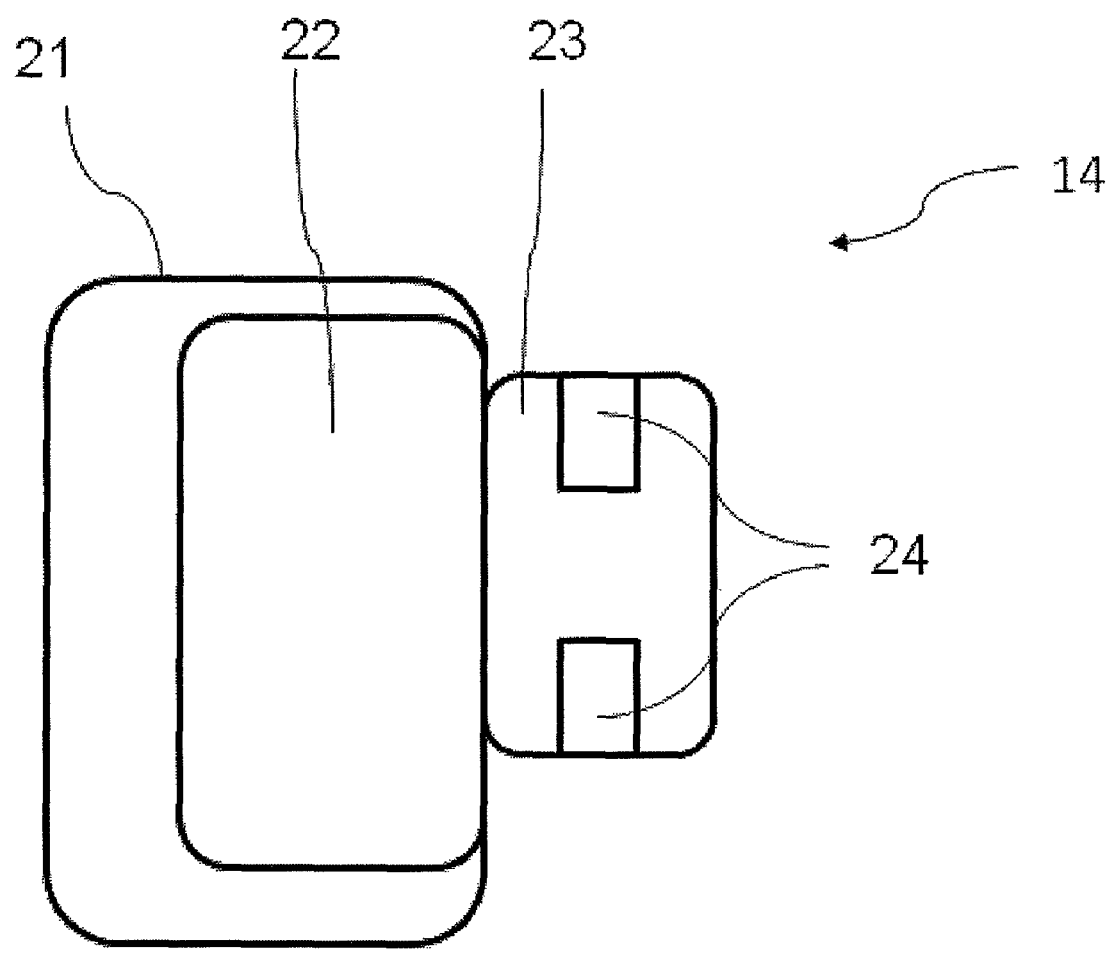
FIG. 2 is a more detailed illustration of the peristaltic pump as provided by the embodiment of FIG. 1.

FIG. 2 provides a cross sectional detailed view of the peristaltic pump 14 as used in conjunction with the embodiment as shown in FIG. 1. As shown in FIG. 2, the peristaltic pump 14 comprises a pump casing 21, a pump motor 22 disposed inside the pump casing 21, and a rotor 23 having one or more rollers 24 such that the portion of tubing to be extruded can become partially secured inside the rotor 23. The rollers 24 are enabled to move over the tubing which can be secured inside the rotor to aspirate and/or dispense a preselected volume of liquid (through the extruded tubing 12). Component 15 can then be retrofitted to dissect and/or seal the remainder of the extruded tubing as needed and disconnect it from the device as appropriate.

FIG. 3 provides a cross sectional view of an alternate embodiment of the present invention. The embodiment shown in FIG. 3 shares several common elements with the embodiment of FIG. 1 as discussed, and therefore some of the referenced numerals are reused as appropriate.

In the illustration of FIG. 3, however, an actuator 39 is disposed in the housing 2 below the interchangeable cartridge 4. This actuator is shown to also have a plurality of components; namely a mechanism 38, a syringe pump 30, and a component 37. Mechanism 38 is enabled to automatically extrude a portion of the tubing from the spool 11. In addition, component 37 is also enabled to cut off at least a portion of the extruded tubing 12 at a first position indicated by numerals 17, and if needed, ultimately move the cut-off portion of the extruded tubing to align with the pump 30, as appropriate, as indicated by numerals 16. Furthermore, in some embodiments, the cut-off portion of the tubing can also be sealed to the syringe pump 30 as needed.

Figure 4:
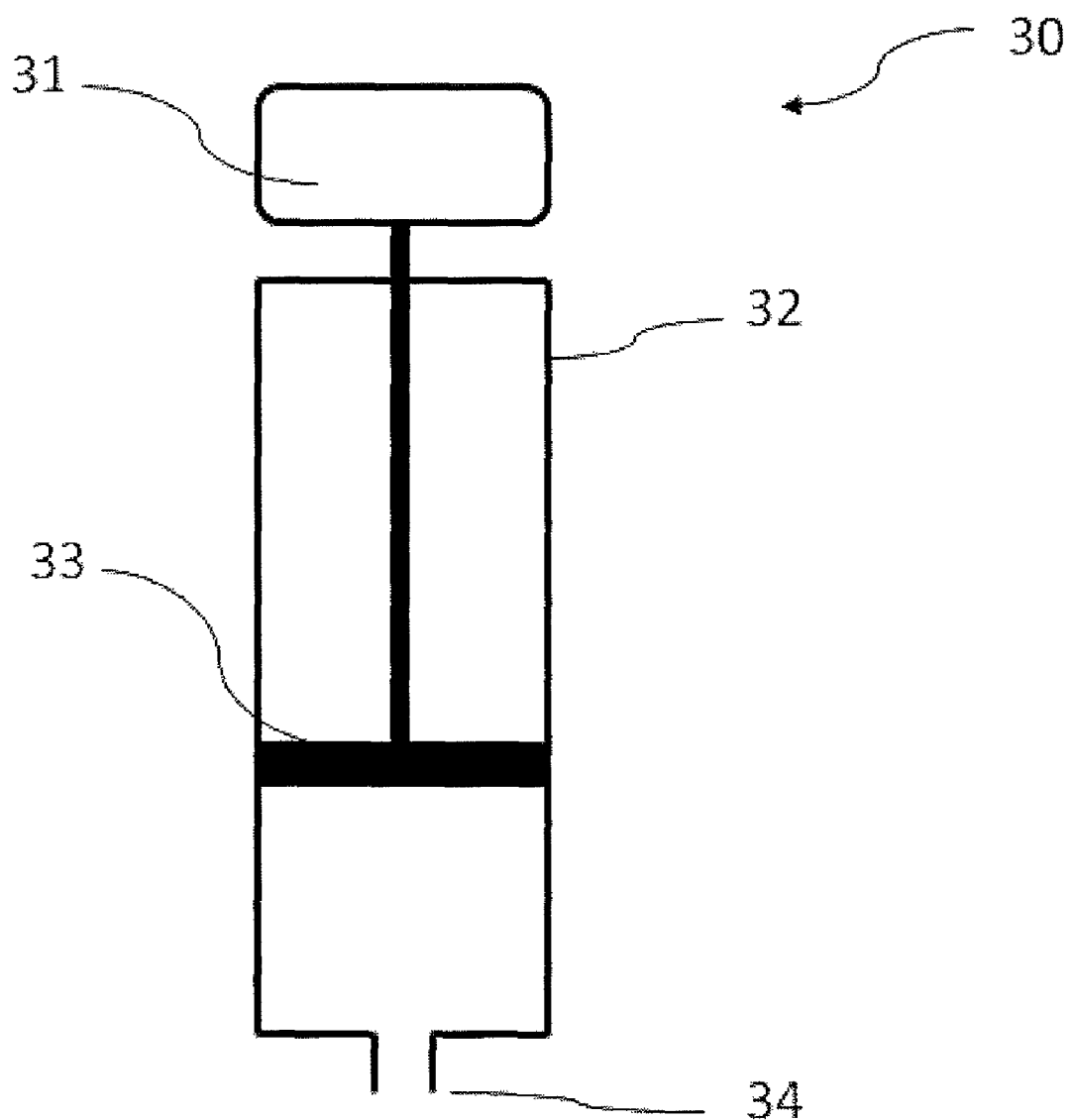
FIG. 4 is a more detailed illustration of the syringe pump as provided by the embodiment of FIG. 3.

FIG. 4 provides a cross sectional illustration of the syringe pump 30 as used in conjunction with the embodiment shown in FIG. 3 in more detail. As shown in FIG. 4, the syringe pump in this embodiment comprises additional components. In the figure shown, the syringe pump 30 includes a syringe driver 31, a barrel 32 having an orifice 34 at one end, and a plunger 33 received in a second end of the barrel 32. Once a portion of tubing in spool 11 is extruded by mechanism 38, component 37 dissects or cuts off at least a portion of the extruded tubing at a first position 17 and seals the cut-off tubing portion to the orifice 34, as indicated by 16. The plunger 33 moves along inside the barrel 32 to aspirate and/or dispense a preselected volume of liquid through tubing 16. Component 37 is also enabled to disconnect tubing 16 from the device as appropriate.

Figure 5:
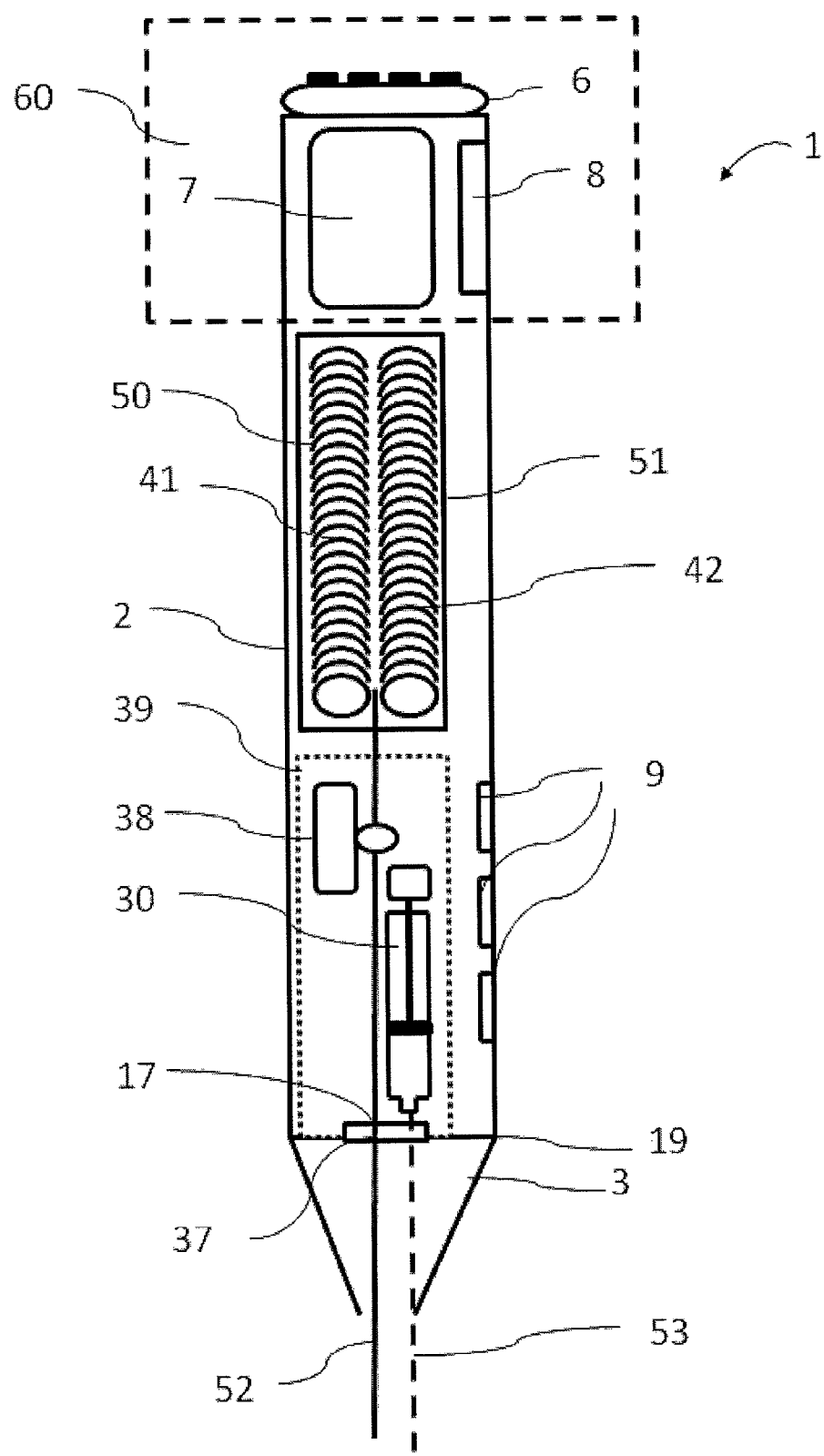
FIG. 5 is a sectional view illustration of another alternate embodiment of the present invention.
Figure 6:
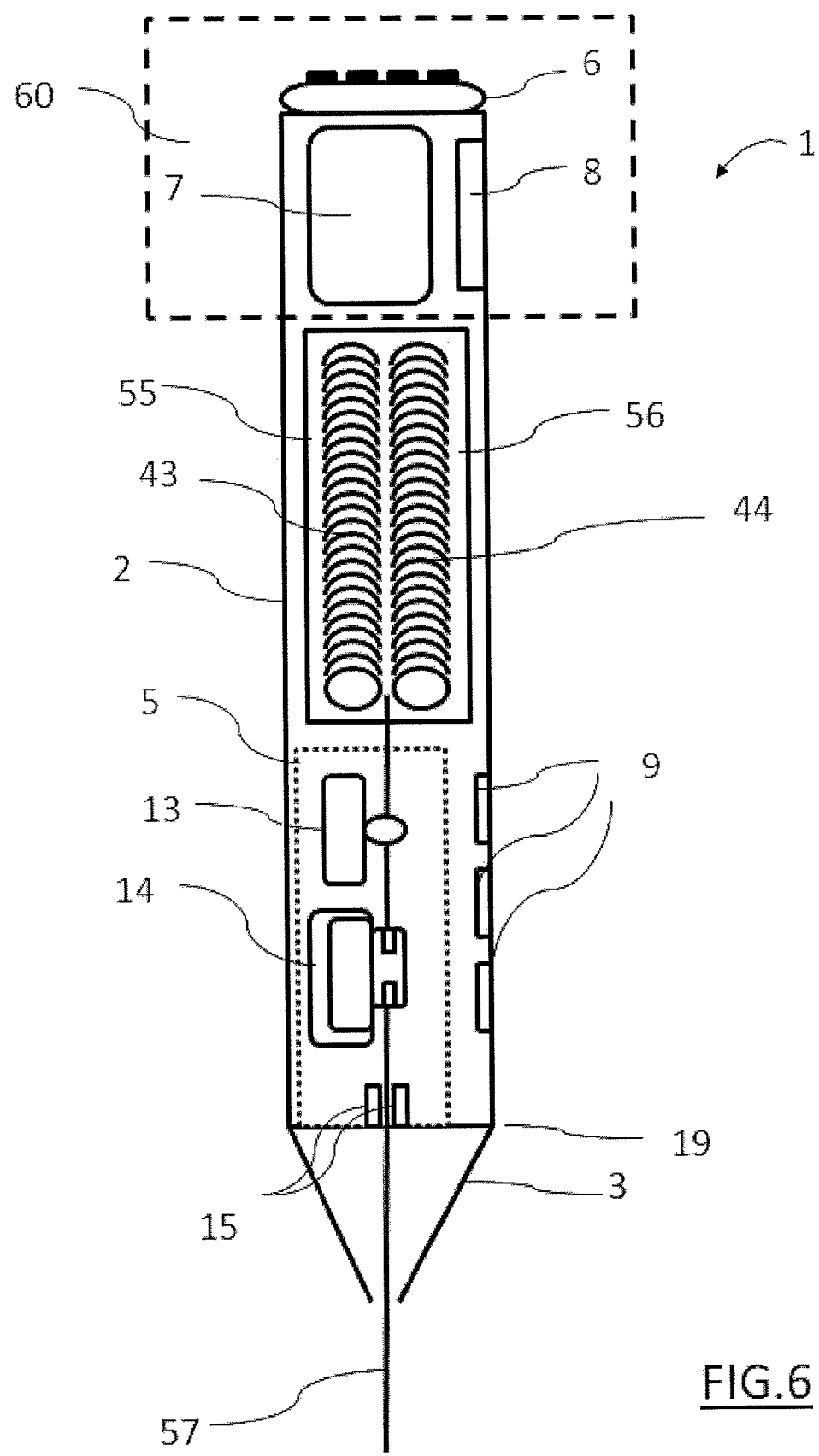
FIG. 6 is a sectional view illustration of yet another alternate embodiment of the present invention.

FIG. 5 and FIG. 6 provide alternate embodiments of the present invention. FIG. 5 and FIG. 6 share several common elements with the embodiments of FIG. 1 and FIG. 3, respectively, and therefore some of the referenced numerals are reused as appropriate. In the cross sectional illustration of the embodiment provided by FIG. 5, the interchangeable cartridge 50 has a holding frame 51 and a plurality of tubing spools that are disposed in the frame 51. Tubing in each spool can have a different inner diameter, length or be made of different materials or have a combination of all or some of the above mentioned characteristic variations. Alternatively one or more tubing can be pretreated with same or different coating of materials. The thickness of such coatings can also be selectively varied such that one spool may include a thin coating of a first substance and a second spool can include a thicker coating of the first or different substance. In the embodiment shown in FIG. 5, as way of example only two spools, 41 and 42 are illustrated. This is done to ease understanding but more spools can be provided in other embodiments as appreciated by those skilled in the art. In each case, the liquid amounts to be aspirated and/or dispensed can be transferred using a pump 30 such as the syringe pump as discussed in conjunction with the embodiments provided by FIG. 3 and FIG. 4.

In the cross sectional illustration of the alternate embodiment of FIG. 6, an interchangeable cartridge 55 has a holding frame 56. Two spools of tubing 43 and 44 are also provided in the frame 56. The embodiment of FIG. 6 is similar in operation to FIG. 5, except that a peristaltic pump 14 as discussed in conjunction with the embodiments provided by FIG. 1 and FIG. 2 is used.

In one embodiment of the present invention, the actuator 5 such as used in conjunction with FIGS. 1-6 can be driven by a control circuit generally shown by box 60 having a power source 7, a display 8, and a memory component 6. The control circuit 60 also includes and/or is in processing communication with actuateable control keys 9. In this embodiment the control keys 9 are disposed outside the general circuit box 60. However, alternate arrangements are possible in other embodiments. The memory component 6, the power source 7, the display 8, and the actuateable control keys 9 are in electrical communication with one other. The control keys 9 allow a user to preselect a range of volumes of liquid to be transferred. The keys 9 can also be used to preselect modes of operation, trigger certain preselected operations, such as aspirating or dispensing, or alternatively select among programs or user-defined operations, and/or to reset operations. In addition, in some embodiments, the time of aspirations and/or dispensations or intervals between aspiration(s) and/or dispensation(s) can be programmable to start or end at certain designated time or time intervals. Display 8 shows user-input commands and selections, or alternatively the status of the operations either in numbers and/or alpha-numerical characters. Information regarding the operation of the device is stored on the memory component 6, which is accessible by the control circuit 60.

In alternate embodiments, the control circuit as shown by box 60 can be a part of an automated system such as a computer or a computing system that includes one or more processors. In some embodiments, as appreciated by those skilled in the art, it is possible for the liquid transferring device to be connected to the automated system such that at a certain time, as preselected by user(s), one or more spools are disposed, if not already included in the device and then a preselected volume of liquids is either aspirated and/or dispensed automatically. This process can then be selectively repeated at selective preset intervals or at set times preselected by the user(s). The type of spool/tubing to be used can also be preselected such that different aspiration/dispensation processes are conducted automatically by spools having different diameters, materials, pretreatments and the like. The automated system or computer can also make a determination to insert or exchange spools of tubing as necessary for each dispensation or aspiration process to be conducted.

As per one embodiment, volumes of liquid to be aspirated and/or dispensed can be preselected by user(s) via the actuateable control keys 9. When a peristaltic pump 14 is included in the actuator, as is described in FIG. 1 and FIG. 6, mechanism 13 is initiated to extrude the tubing to a length able to accommodate the preselected volume and pinch the extruded tubing 12 once a desired length is extruded. In this way, the extruded tubing is isolated and sealed from the spool. The length to be extruded is calculated by the memory component 6 based on the preselected volume and the inner diameter of the tubing being extruded. The preselected volume of liquid is aspirated and/or dispensed by moving the rollers 24 over the tubing secured inside the rotor of the peristaltic pump. After transferring the liquid, the extruded tubing is disconnected from the device by component 15. Each above operation is triggered via the actuateable control keys 9. The display 8 allows a user to monitor the status of each operation and to also look up operating parameters for previous operations.

In another embodiment, in order to aspirate or dispense liquids using a syringe pump, as shown in FIG. 3 and FIG. 5, the volume of liquid to be aspirated and/or dispensed is preselected by user(s) via the actuateable control keys 9. Mechanism 38 is initiated to extrude the tubing to a length able to accommodate the preselected volume. The length to be extruded can be calculated, as per one embodiment, by the memory component 6 based on the preselected volume and inner diameter of tubing being extruded. The extruded tubing is cut off from the remaining spool by component 37 and the cut-off portion of the extruded tubing is sealed to the syringe pump at its orifice. The preselected volume of liquid is aspirated and/or dispensed by the movement of the plunger inside of the syringe pump. After transferring the liquid, the cut-off portion of the extruded tubing can be disconnected from the device by component 37. Similarly, each above operation is triggered via the actuateable control keys 9. The display 8 allows a user to monitor the status of each operation of the above process, and to look up operating parameters for previous operations.

While the invention has been described in accordance with certain preferred embodiments thereof, those skilled in the art will understand the many modifications and enhancements which can be made thereto without departing from the true scope and spirit of the invention, which is limited only by the claims appended below.

What is claimed is:

1. A device for automatically aspirating and/or dispensing liquids with precision, comprising:
   a housing having an opening at a lower end with a fixed tip protruding out of said lower end;
   an interchangeable cartridge disposed inside said housing, said cartridge having:
   a holding frame; and
   a spool of tubing provided in said frame such that one end of said tubing is aligned with said tip; and
   an actuator enabled to automatically extrude at least part of said tubing so as to accommodate a preselected volume of liquid, said actuator further enabled to aspirate and/or dispense said liquid through said extruded tubing, and disconnect said extruded tubing from said device.

2. The device as set forth in claim 1, wherein said tubing comprises a first inner diameter or a second inner diameter.

3. The device as set forth in claim 1, wherein said tubing is made substantially of plastic or plastic components.

4. The device as set forth in claim 1, wherein said cartridge comprises tubing of both first and second inner diameters which can be alternatively selected.

5. The device as set forth in claim 1, wherein said tubing is made of different materials.

6. The device as set forth in claim 1, wherein said tubing is able to be pressed to a flat form when rolled in said spool, and is able to form a tubular form when extruded.

7. The device as set forth in claim 1, wherein said tubing is internally pretreated.

8. The device as set forth in claim 1, wherein said cartridge can have multiple spools of tubing with different characteristics that can be alternatively selected.

9. The device as set forth in claim 8, wherein said tubing characteristics include variety of inner diameters, fabrication materials and inner pretreatments.

10. The device as set forth in claim 1, further comprising a control circuit, operable to drive said actuator, said control circuit having:
    a power source;
    a plurality of actuateable control keys in electrical communication with said control circuit and enabled to preselect modes of operation and allow a user to preselect volumes and set up a time for liquid to be aspirated and/or dispensed;
    a display for displaying numbers and/or alpha-numerical characters; and
    a memory component for storing data accessible by said control circuit to enable preselected operations.

11. The device as set forth in claim 10 wherein said control keys are enabled to trigger preselected operations, program user-defined operations, and reset controlling operations.

12. The device as set forth in claim 10, wherein said control circuit is provided in a computer having a processor such that said computer can automatically dispense and aspire a volume of liquid at a certain time from a spool of tubing having a certain preselected characteristic; said computer enabled to automatically insert or exchange tubing spools as necessary.

13. The device as set forth in claim 1, wherein said actuator comprises:
- a mechanism for automatically extruding said tubing to a first length enabled to accommodate a preselected volume of liquid; said mechanism also enabled to pinch said extruded tubing from remaining spool once said first length is achieved;
- a pump for aspirating and/or dispensing liquids through said extruded tubing; and
- a component for cutting off and disconnecting said extruded tubing from said device.

14. The device as set forth in claim 13 wherein said pump is a peristaltic pump further comprising: a pump casing, a pump motor and a rotor with a plurality of rollers such that a portion of said spool of tubing is partially secured inside said rotor, and said rollers are enabled to move over said portion of tubing secured inside to aspirate and/or dispense said preselected volume of liquid.

15. The device as set forth in claim 1, wherein said actuator comprises:
- a mechanism for automatically extruding said tubing to a first length enabled to accommodate a preselected volume of liquid;
- a pump for aspirating and/or dispensing liquids; and
- a component for cutting off said extruded tubing, and sealing said cut-off extruded tubing to said pump; said component also enabled to disconnect said cut-off extruded tubing from said device.

16. The device as set forth in claim 15, wherein said pump is a syringe pump further comprising:
- a syringe driver;
- a barrel having an orifice at one end; and
- a plunger received in the other end of said barrel enabled to move along inside said barrel to aspirate and/or dispense said preselected volume of liquid.

17. The device as set forth in claim 16, wherein said orifice can be aligned, connected and sealed with said cut-off tubing inside said housing.

* * * * *